United States Patent
Will et al.

(10) Patent No.: US 11,145,390 B2
(45) Date of Patent: Oct. 12, 2021

(54) METHODS AND SYSTEMS FOR RECOMMENDING FILTERS TO APPLY TO CLINICAL TRIAL SEARCH RESULTS USING MACHINE LEARNING TECHNIQUES

(71) Applicant: International Business Machines Corporation, Armonk, NY (US)

(72) Inventors: Eric W Will, Rochester, MN (US); Adam Clark, Mantorville, MN (US); Kimberly Diane Kenna, Cary, NC (US)

(73) Assignee: International Business Machines Corporation, Armonk, NY (US)

( * ) Notice: Subject to any disclaimer, the term of this patent is extended or adjusted under 35 U.S.C. 154(b) by 207 days.

(21) Appl. No.: 16/273,750

(22) Filed: Feb. 12, 2019

(65) Prior Publication Data
US 2020/0258600 A1    Aug. 13, 2020

(51) Int. Cl.
*G16H 10/60* (2018.01)
*G16H 10/20* (2018.01)
(Continued)

(52) U.S. Cl.
CPC ............ *G16H 10/20* (2018.01); *G06N 20/20* (2019.01); *G16H 10/60* (2018.01); *G16H 50/70* (2018.01)

(58) Field of Classification Search
CPC .. C12Q 2600/106; G16H 10/60; G16H 10/20; G16H 10/40; G16H 50/70; G16H 20/10; G16H 40/67; G16B 40/20; G16B 5/20; G06F 21/6245; G06N 20/00; G06N 20/20; G06N 3/0445; G06N 3/08
(Continued)

(56) References Cited

U.S. PATENT DOCUMENTS

2014/0122113 A1    5/2014  Hoffman, Jr. et al.
2014/0303999 A1 *  10/2014 Efros ..................... G16H 15/00
                                            705/2
(Continued)

FOREIGN PATENT DOCUMENTS

WO       2016203457 A1     12/2016
WO  WO 2020/172131 A1 *    2/2019 ............. G16H 10/20

OTHER PUBLICATIONS

Chintan Patel, James Cimino, Julian Dolby, Achille Fokoue, Aditya Kalyanpur, Aaron Kershenbaum, Li Ma, Edith Schonberg, and Kavitha Srinivas; Matching Patient Records to Clinical Trials Using Ontologies, ISWC/ASWC 2007, LNCS 4825, vol. 4825; pp. 816-829. (Year: 2007).*

*Primary Examiner* — Elaine Gort
*Assistant Examiner* — Teresa S Williams
(74) *Attorney, Agent, or Firm* — Patterson + Sheridan, LLP (57) ABSTRACT

A method and apparatus for filtering clinical trials using machine learning techniques is disclosed. An example method generally includes receiving a first set of filters that were applied to a first plurality of clinical trials with respect to a first patient. A system determines one or more attributes of the first patient and trains a machine learning (ML) model based on the first set of filters and the one or more attributes of the first patient. The system receives a selection of a second patient, determines one or more attributes of the second patient, and generates a second set of filters by processing the one or more attributes of the second patient using the trained ML model.

20 Claims, 5 Drawing Sheets

(51) Int. Cl.
*G06N 20/20* (2019.01)
*G16H 50/70* (2018.01)

(58) Field of Classification Search
USPC .............................................. 705/3
See application file for complete search history.

(56) References Cited

U.S. PATENT DOCUMENTS

| | | | |
|---|---|---|---|
| 2015/0161336 A1* | 6/2015 | Kalathil | G16H 10/60 |
| | | | 705/3 |
| 2017/0351816 A1 | 12/2017 | Fink et al. | |
| 2018/0046780 A1 | 2/2018 | Graiver et al. | |
| 2019/0272907 A1* | 9/2019 | Aldairy | G06F 40/279 |
| 2020/0234801 A1* | 7/2020 | Mao | G16H 10/20 |

\* cited by examiner

| PatientID | Condition | Stage | PreviousProcedures | PrescribedMedication |
|---|---|---|---|---|
| 1234 | Pancreatic Cancer | III | Whipple procedure, radiation therapy | gemcitabine |

PATIENT MEDICAL DATA 410

| PatientID | FilterID |
|---|---|
| 1234 | 0f5a309e |
| 1234 | 045229b9 |
| 1234 | cd50cd5b |

FILTER HISTORY DATA 420

( [Pancreatic Cancer, III, {Whipple procedure, radiation therapy}, gemcitabine] {0f5a309e, 045229b9, cd50cd5b} )

VECTOR 430

METHODS AND SYSTEMS FOR RECOMMENDING FILTERS TO APPLY TO CLINICAL TRIAL SEARCH RESULTS USING MACHINE LEARNING TECHNIQUES

BACKGROUND

The present disclosure relates to using machine learning techniques to deliver clinical trial recommendations, and more specifically, to recommending filters to apply to search results to refine a set of potentially relevant clinical trials for a patient.

Clinical trials in medicine are research studies that are used to test and evaluate various medical treatments, drugs, or devices under development. Typically, clinical trials are defined as a treatment, drug, or device being developed, eligibility criteria (or inclusion criteria) defining the characteristics of patients who may be eligible to participate in a specified trial, and disqualifying criteria defining the characteristics of patients who are not eligible for participation in the trial. For example, the eligibility criteria may include the medical condition that the subject of the clinical trial is addressing, a stage of medical treatment that patients should be at, what previous treatments a patient may have received prior to entering the clinical trial, and the like. The disqualifying criteria defining the characteristics of patients who are not eligible to participate in a specified trial may include, for example, a stage of a disease beyond which a patient would be ineligible for inclusion in the trial, previous treatments that disqualify a patient from participating in the trial, and the like. While clinical trial eligibility and disqualifying criteria may be written according to a standard format, the eligibility and disqualifying criteria and other relevant information about clinical trials may not be written in a clear and concise manner.

At any given time, a patient may potentially be eligible for participation in a variety of clinical trials. Typically, to determine what clinical trial(s) a patient may be eligible for participation in, the patient's doctors and/or other clinical staff may review the patient's medical records and the eligibility and disqualifying criteria for a number of clinical trials to identify trials that may be of interest to the patient. However, the process of identifying trials that are potentially of interest for the patient may be a time consuming, manual process that requires doctors or other clinical staff to compare potentially voluminous patient records with at least the eligibility and disqualifying criteria for each clinical trial. Further, due to the number and wide variety of clinical trials that may be active at any time, manual searches for trials of interest may miss potentially relevant trials for a given patient. In some cases, manual analysis of potential clinical trials to enroll a patient in may rely on institutional procedures that prioritize clinical trials being run in certain institutions over potentially relevant clinical trials run in other institutions, which may result in potentially relevant clinical trials for a patient being overlooked or otherwise omitted from consideration.

Automated methods for analyzing patient records and clinical trial definitions may not be able to accurately match patients with the clinical trials that patients may be eligible to participate in for various reasons. For example, automated methods may not be able to accurately parse the intent of statements in a clinical trial definition. In another example, automated methods may not be able to understand the implications of a patient's records with respect to the ability to successfully complete a clinical trial. In still further examples, automated methods may be unable to determine or identify temporal relationships associated with eligibility or disqualifying criteria for a clinical trial.

SUMMARY

One embodiment disclosed herein includes a method for cognitive clinical trial filtration. The method generally includes receiving a first set of filters that were applied to a first plurality of clinical trials with respect to a first patient. A system determines one or more attributes of the first patient and trains a machine learning (ML) model based on the first set of filters and the one or more attributes of the first patient. The system receives a selection of a second patient, determines one or more attributes of the second patient, and generates a second set of filters by processing the one or more attributes of the second patient using the trained ML model.

Another embodiment includes a processor and a memory having instructions stored thereon which, when executed by the processor, performs an operation for cognitive clinical trial filtration. The operation generally includes receiving a first set of filters that were applied to a first plurality of clinical trials with respect to a first patient. A system determines one or more attributes of the first patient and trains a machine learning (ML) model based on the first set of filters and the one or more attributes of the first patient. The system receives a selection of a second patient, determines one or more attributes of the second patient, and generates a second set of filters by processing the one or more attributes of the second patient using the trained ML model.

Still another embodiment includes a computer-readable storage medium having instructions stored thereon, which, when executed on a processor, performs an operation for cognitive clinical trial filtration. The operation generally includes receiving a first set of filters that were applied to a first plurality of clinical trials with respect to a first patient. A system determines one or more attributes of the first patient and trains a machine learning (ML) model based on the first set of filters and the one or more attributes of the first patient. The system receives a selection of a second patient, determines one or more attributes of the second patient, and generates a second set of filters by processing the one or more attributes of the second patient using the trained ML model.

DETAILED DESCRIPTION

Embodiments presented herein describe techniques for recommending search filters to apply to result sets of clinical trials that may be relevant to a given patient to further refine a set of potentially relevant clinical trials for the patient. As discussed, at any given time, a large number of trials directed to treating a given medical condition with diverse eligibility and disqualifying criteria and operational characteristics may be open for enrollment at any given time. However, due to the large number of trials that may be open for enrollment, the diverse criteria of these trials, and unique patient characteristics, filtering trials directed to treating a given medical condition may generally be a manual and unguided process. The manual and unguided process of manually applying (and discarding) filters to a result set of potentially relevant clinical trials may be a time consuming process for each patient. Further, manual and unguided application of filters to a result set of potentially relevant clinical trials may be inaccurate, as a user may make mistakes when examining clinical trial criteria and operational characteristics against patient medical data, accidentally apply or remove filters, or otherwise erroneously interact with a result data set.

As discussed herein, the recommendations of filters to apply to sets of clinical trials that may be relevant to a given patient may be developed by learning from user interactions with a clinical trial search system while the user is attempting to identify potentially relevant clinical trials to recommend to a patient. As used herein, a filter generally refers to additional criteria that may be applied to a set of search results (i.e., potentially relevant clinical trials) to further refine the set of search results. By recommending filters to apply to a set of potentially relevant clinical trials using learned behaviors of other users, techniques described herein may accelerate the process of searching for potentially relevant clinical trials for a patient. Further, by recommending filters to apply to a set of potentially relevant clinical trials, embodiments discussed herein may reduce the amount of processing resources, network bandwidth, and other computing resources used in searching for relevant clinical trials for a given patient by recommending the application of filters that similar users have also used (indicating that these filters have been found to be useful in identifying relevant clinical trials for a given patient) and avoiding the application of filters that are likely to not be useful. Filters that are computationally expensive to apply to a result data set of potentially relevant clinical trials and are likely to be useful to a clinician in identifying relevant clinical trials for a patient may be recommended, or even automatically applied. Meanwhile, filters that are computationally expensive to apply to the result data set and unlikely to be useful to the clinician may not be recommended to the clinician to reduce the likelihood that the clinician will attempt to apply these filters to the result data set and potentially waste computing resources in doing so. Further, the recommendation of filters to apply to a set of potentially relevant clinical trials may accurately match highly qualified patients to relevant clinical trials, which may result in better trial outcomes and may rapidly advance medical technology.

Figure 1:
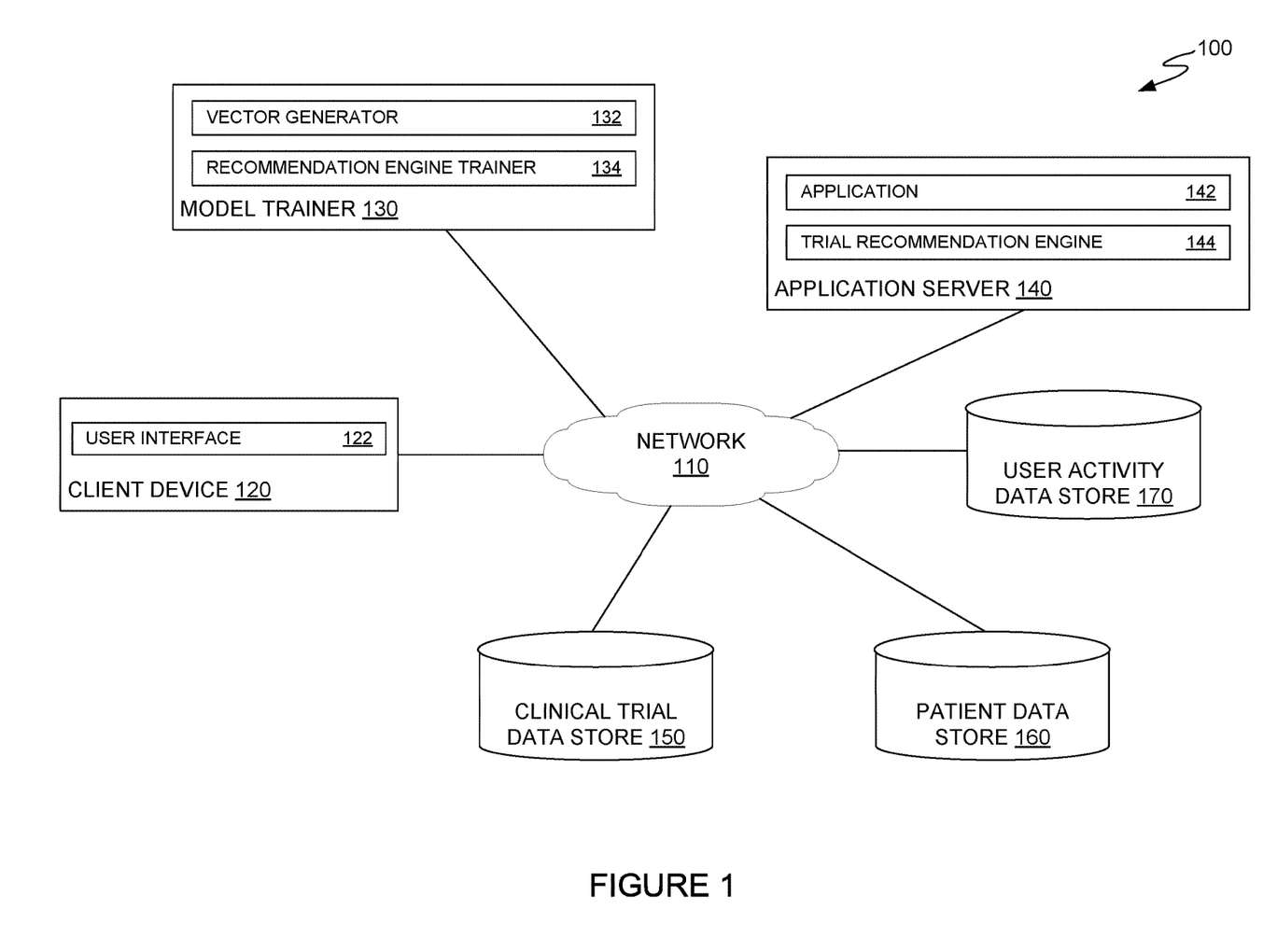
FIG. 1 illustrates an example networked environment in which machine learning models are used to deliver clinical trial recommendations based on patient medical records and clinical trial definitions, according to one embodiment.

FIG. 1 illustrates an example networked computing environment in which machine learning models are used to recommend clinical trials for a patient based on patient medical history and clinical trial characteristics, according to an embodiment of the present disclosure. As illustrated, computing environment 100 includes a client device 120, a model trainer 130, an application server 140, a clinical trial data store 150, a patient data store 160, and a user activity store 170, connected via network 110.

Client device 120 generally is representative of a computing device on which a user can define and/or manage the training of predictive models used by trial recommendation engine 144 to recommend potentially relevant clinical trials for a patient and access application 142 on application server 140 to obtain a set of potentially relevant clinical trials for a patient. Client device 120 may be, for example, a laptop computer, a desktop computer, a thin client, a tablet computer, a mobile computing device, and the like. As illustrated, client device 120 includes a user interface 122. User interface 122 allows a user of client device 120 to define a training data set for use in training machine learning models for recommending relevant clinical trials to a user as described in further detail herein. The training data set may include a first set of labeled data used to train the machine learning models and a second set of unlabeled data used to verify the accuracy of the trained machine learning models and refine the trained machine learning models prior to deployment to trial recommendation service 140. User interface 122 additionally allows a user of client device 120 to initiate a search for recommended clinical trials that may be of interest to a patient by providing, to trial recommendation service 140, the patient's medical records in a request for one or more potentially relevant clinical trials to present to a patient.

Model trainer 130 generally uses information about patients previously enrolled in trials and the criteria defined for those trials to train one or more machine learning models used in recommending clinical trials that are potentially relevant to a particular patient. As illustrated, model trainer 130 includes a vector generator 132 and a recommendation engine trainer 134.

Vector generator 132 is generally configured to generate a training data set for use by recommendation engine trainer 134 to train a machine learning model for recommending potentially relevant clinical trials to a user based on patient medical history. To generate the training data set, vector generator 132 can obtain information about previously completed from clinical trial data store 150 and patient medical history data from patient data store 160. The information obtained from clinical trial data store 150 may include, for example, a roster of patients enrolled in a specific clinical trial and a definition of that clinical trial. The definition of the clinical trial may include eligibility and disqualifying criteria, patient requirements for participation in the trial, a trial enrollment deadline, and other information defining the clinical trial. The roster of patients may include information identifying each patient that vector generator 132 can use to obtain patient medical records from patient data store 160.

To generate the training data to be used by clinical trial recommendation trainer 134, vector generator can generate a first set of training data comprising feature data and label data used to train a machine learning model and a second set of unlabeled feature data that can be used to test the generated machine learning model. For example, in an embodiment where machine learning techniques are used to recommend relevant trials for a patient, the first set of data may comprise a plurality of vectors, where the features in each vector include information from patient medical records, and the labels in each vector include the characteristics of a given clinical trial (e.g., eligibility criteria and disqualifying criteria defined for a clinical trial). The second set of data may comprise an unlabeled set of patient medical records associated with patients who have been accepted into a clinical trial.

In some embodiments, the features in the first set of data may further include additional data that may be used to further refine recommendations of trials that may be relevant to a patient. This additional data may include, for example, information about a current stage of treatment that a patient is in, the specialty of the patient's clinicians, the institution that is treating the patient, and patient completion success for other trials that the patient may have participated in. These additional features may be used to further refine the recommendations delivered by trial recommendation engine 144 to deliver more relevant recommendations to the patient's doctors. For example, the use of information about a stage of treatment that the patient is in may be used to prioritize recommendations of trials relevant to that particular stage of treatment over trials relevant to earlier or later stages of treatment (e.g., where a patient is in an early stage of a disease, prioritizing clinical trials directed to curative treatments over palliative treatments that are more appropriate for patients with later or terminal stages of the disease). Likewise, using information about the patient's clinicians may further indicate, at least implicitly, relevant information about the patient's conditions, such as disease progression, that may be used to prioritize some clinical trials over others. This information may, for example, prioritize clinical trials being held at particular institutions (e.g., based on a distance metric from the patient's clinicians) based on assumptions that patients are more likely to successfully participate in trials that are more easily accessible to the patient. Finally, information about the patient's previous trial completion success may be used as an input to prioritize trials, for example, with similar or less stringent completion requirements to trials that the patient has previously successfully participated in. It should be noted, however, that these additional data points for refining the recommendation of relevant trials is not exhaustive, and other appropriate data points may be used to train predictive models for delivering recommendations of potentially relevant clinical trials for a given user.

In some embodiments, vector generator 132 may additionally generate a second training data set to use in identifying filters to apply to a set of potentially relevant clinical trials to further refine the recommended set of potentially relevant clinical trials to deliver to a user of application 142. The second training data set may be generated from user activity data stored in user activity data store 170 for clinicians associated with a given institution as well as for a particular clinician's preferences to identify a set of preferences over time for filtering clinical trials for different cohorts of patients. When a user initiates a search for potentially relevant clinical trials, application 142 can record filtering activity of the user to identify one or more filters that the user has applied to an initial set of potentially relevant clinical trials. The recorded filtering activity may be saved as time-series data at user activity data store 170 associating a user with patient characteristics and the one or more applied filters a user used to refine the set of potentially relevant clinical trials displayed by application 142. The one or more filters may include, without limitation, specific types of trials (e.g., to select early or later phase trials), trials with matching characteristics, trials with specific operating characteristics (e.g., location of the trial, a number of patients to be enrolled in a trial, competitive studies at the same location or nearby locations, etc.), likelihood of completion based on similar trials, and the like. Based on the applied filters, vector generator 132 can generate one or more vectors associating the patient data and applied filters with trial characteristics for the one or more clinical trials that were deemed potentially relevant and matched the filter criteria defined by the applied filters. It should be recognized that other contextual information, in addition to previously applied filters, may be used to generate the vectors in the second training data set.

Still further, some embodiments may additionally include characteristics of one or more clinical trials in the second training data set to further refine the sets of filters recommended to a user. The one or more clinical trials used for the inclusion of trial characteristics into the second training data set may, for example, include trials that a patient was enrolled in, trials flagged as potentially relevant by the patient's clinicians, trials that a patient enrolled in and successfully completed, and so on. The characteristics of the one or more clinical trials may include, for example, a location of the clinical trial, other clinical trials located at the site, and other trial characteristics that may be predictive of whether a clinical trial is relevant to a patient. A predictive model trained using this second training data set may thus be configured to recommend the application of filters to an initial set of relevant clinical trials based on the various operational characteristics of the trial.

As discussed herein, the vectors generated by vector generator 132 for the first and second training data sets may be generated using a variety of techniques. In some embodiments, the vectors may be generated from a corpus of clinical trials using natural language processing (NLP) techniques such as the Bag of Words Model or Term Frequency and Inverse Document Frequency (TD-IDF) Model. Other NLP techniques, such as the word2vec algorithm or other neural network-based algorithms, may also be used to create vectors for the first and second training data sets. Additionally, key concepts, logical parse, key criterion triggers, and other non-NLP techniques may be used to generate vectors from corpuses of clinical trials. Criterion triggers may include, for example, hypothetical spans, negations, ignorable passages, and other criteria that may be used to identify relevant information in a clinical trial specification to be included in a vector.

Recommendation engine trainer 134 generally is configured to obtain the training data generated by vector generator 132 and, using supervised learning techniques, train one or more predictive models for delivering recommendations of potentially relevant clinical trials for a patient.

In some embodiments, recommendation engine trainer 134 may train a first machine learning model used to identify an initial set of clinical trials that are likely to be relevant to a patient based on patient medical data and the characteristics of each clinical trial (e.g., eligibility and exclusion criteria). To train the first machine learning model, recommendation engine trainer 134 can utilize supervised learning techniques using the first training data set discussed above. The labeled data in the first training data set may be used to initially train the first machine learning model, and a user may test the initially trained first machine learning model using the unlabeled data in the first training data set to verify that the first machine learning model returns accurate results (e.g., a recommended set of clinical trials including one or more trials that a patient actually enrolled in) and, if needed, further refine the trained machine learning model based on real-life clinical trial enrollment data associated with a given patient in the unlabeled data.

Recommendation engine trainer 134 may further be configured to train a second machine learning model to recommend filters or orders of filters to apply to a result set of potentially relevant clinical trials for a patient. The use of the recommended filters or order of filters to apply may be used to further refine the set of clinical trials to present to a patient for further consideration. In some embodiments, the second machine learning model may be trained using supervised learning techniques using a training data set with patient attributes (e.g., patient medical condition being treated, stage of treatment, previously performed medical procedures, medications currently prescribed to the patient, etc.) used as feature data and the time-sequence data of filters applied to a result data set used as label data, as discussed above.

In some embodiments, the machine learning models may be implemented as recurrent neural networks (RNNs) or other regression algorithms that return a probability distribution representing the likelihood that a specific clinical trial or search filter will be relevant to a patient and/or clinician treating the patient. RNN may be used, as these networks may be able to support sequential input such as words in a sentence in a clinical trial definition and parse out relevant information from these sentences. By using an RNN, the machine learning model may be configured to make predictions based on one or more of patient medical information (e.g., a condition under treatment, the stage of the condition under treatment, visit periodicity, previous medical procedures performed on the patient to treat the condition, medications prescribed to treat the condition, etc.), clinician information (e.g., affiliated institution, specialty, etc.), and other information that may be used as feature data in the vectors described above. When the first machine learning model is provided an input of patient medical information for analysis, the first machine learning model may generate an output of a set of probability scores for each clinical trial in a set of clinical trials. The generated probability score for a particular clinical trial in the set of clinical trials generally represents a likelihood that the clinical trial will be relevant to the patient in view of the patient's medical information. When the second machine learning model is provided an input of at least patient medical information for analysis (and, optionally, clinician information (e.g., institutional affiliation, specialty, etc.), clinical trial operational data, and other relevant information), the second machine learning model may generate an output of a set of probability scores for each filter that a user could apply to refine a set of potentially relevant clinical trials for a patient. In refining the set of potentially relevant clinical trials, the filters may be applied such that the set of potentially relevant clinical trials include the clinical trials that the user believes would be beneficial to the patient (e.g., in terms of prolonged symptom-free survival, palliative care, curative options, etc.) and that the patient would be eligible to participate in.

Each filter that a user can apply to a set of potentially relevant clinical trials (e.g., returned by the first machine learning model in response to a request for potentially relevant clinical trials based on patient medical information for a particular patient) may be associated with a unique identifier (e.g., a Globally Unique Identifier (GUID), a hash of the text associated with the filter, or other unique identifier). When a user applies a filter to the set of potentially relevant clinical trials, a tracking system can generate a record in user activity data store 170 reflecting the user's application of the filter to the set of potentially relevant clinical trials. Each record stored in user activity data store 170 may include one or more filters applied to the set of potentially relevant clinical trials for a given search session (e.g., for a specific patient for whom the user is searching for relevant clinical trials for enrollment). As discussed, the user activity (e.g., applied filters) may be included as labels of vectors including at least patient medical information as features, and these vectors may be used to train the second machine learning model used by trial recommendation engine 144 for recommending (and, in some embodiments, automatically applying) relevant filters for refining the set of potentially relevant clinical trials retrieved by application 142.

While the above description refers to the use of regressive algorithms for training the machine learning models described herein, it should be recognized that classification type algorithms, where the output of a trained machine learning model is an identified category, may also be used to identify types of clinical trials that a user may be eligible for participation in and types of filters to use in refining a set of potentially relevant clinical trials for the patient.

Application server 140 generally includes an application 142 and a trial recommendation engine 144. Application 142 may be any type of application in which users can request recommendations of potentially relevant clinical trials for a patient by providing patient data (e.g., medical condition information, treatment history, prior clinical trial participation history, and other relevant information) and, in some embodiments, user-defined filters in a search request executed by application 142. Client device 120 may instantiate or initiate a session of application 142 in response to a request for application content (e.g., a list of active clinical trials that are enrolling patients for participation) generated by a user of client device 120. In some embodiments, the instance of a session of application 142 may be instantiated by a user of client device 120 accessing a home page of an application 142 structured as a web application. In other embodiments, user interface 122 may instantiate the instance of application 142 by launching an executable file on client device that includes components that execute locally on client device 120 and use data provided by application 142.

During execution of application 142, a user may request a set of recommended clinical trials for a given patient by providing that patient's medical data to application 142 in conjunction with a search request. In response, application 142 provides the received medical data to trial recommendation engine 144 for analysis. Application 142 may receive a list of potentially relevant clinical trials for the patient from trial recommendation engine, as discussed in further detail below, and display the list of potentially relevant clinical trials in user interface 122 of client device 120. In some embodiments, the list of potentially relevant clinical trials may include a predetermined number of potentially relevant clinical trials for the patient and may be sorted based on the predictive scores associated with each of clinical trial in the list of potentially relevant clinical trials. Application 142 may additionally allow a user of client device 120 to further refine the list of potentially relevant clinical trials using one or more user-defined filters.

Trial recommendation engine 144 uses the machine learning model generated by recommendation engine trainer using the first training data set 134 to examine medical records for a given patient and recommend potentially relevant clinical trials for the patient to the patient's clinicians based, at least in part, on the patient's medical history. Techniques for doing so are described in U.S. patent application Ser. No. 16/260,382 of Clark et al., filed Jan. 29, 2019 and entitled "Intelligent Ranking of Trials for a Patient", the contents of which are herein incorporated by reference.

The set of results generated by trial recommendation engine 144 may be considered a base result set including potentially relevant clinical trials for the patient, and one or more filters may be applied to the base result set to further refine the set of results and deliver a recommendation of a number of relevant clinical trials for the patient using one or more recommended filters. To refine the base result set identify the recommended filters to apply to the set of results generated by trial recommendation engine 144, trial recommendation engine 144 may request a set of filters from the second machine learning model generated by recommendation engine trainer 134 (e.g., the machine learning model trained using the second data set of patient medical information and, in some embodiments, additional information as features and the applied filters as labels). In response, trial recommendation engine 144 may receive a probability distribution over a set of filters that can be applied to the base result set to refine the clinical trials to be displayed to a user of application 142. The probability distribution generally reflects a likelihood, learned from the interactions of similar users searching for clinical trials to enroll similar patients into, that each filter will be useful in narrowing the base result set into a set of highly relevant clinical trials (e.g., trials that address the medical condition the patient is being treated for, are relevant to the stage of the medical condition the patient is in, are likely to accept the patient into the trial, and are relevant for the user of application 142 (e.g., to reflect institutional preferences, previous experiences of successful and unsuccessful trials, etc.)). A high probability value may indicate that a large number of clinicians have applied the filter to the base result set of potentially relevant clinical trials generated for similar patients, while lower probability values may indicate that fewer clinicians have applied the filter to the base result set of potentially relevant clinical trials generated for similar patients.

In some embodiments, one or more filters included in the set of filters may be automatically applied to the base result set including potentially relevant clinical trials for the patient in order to narrow the set of clinical trials presented to the user of application 142. To determine which filters may be automatically applied to the base result set, trial recommendation engine 144 may examine the probability distribution returned by the second machine learning model to identify filters having a probability score exceeding a threshold value. The threshold value may represent a likelihood that a specific filter has been applied to search results generated for a specific type of patient (e.g., a patient being treated for the same or similar medical condition, at the same stage of the condition, with similar treatment and medication histories, and so on) by similar clinicians (e.g., clinicians affiliated with the same institution, practicing the same specialty, and so on). The probability threshold value may be set such that filters applied by most or all clinicians in the training data set for the specific type of patient are automatically applied to the base result set generated by trial recommendation engine 144. By automatically applying these high-probability filters, trial recommendation engine 144 may automatically deliver a more relevant and focused set of clinical trials to the user for discussion with the patient. The clinical trials in the filtered set generated by trial recommendation engine may, for example, represent trials with similar characteristics as trials that other clinicians have searched for and potentially enrolled patients in.

In some embodiments, the set of filters (or a subset of the filtered set having the n highest probability scores) may be adjusted based on the number of trials remaining in the filtered set of trials after application of each filter to the base result set. Trial recommendation engine 144 may execute a number of filters remaining in filtered base result set and record the number of results remaining after execution of each of the filters. Filters for which no results remain may be dropped from the set of filters. The remaining filters may be ranked based, at least in part, on the number of remaining clinical trials in the set of potentially relevant clinical trials after application of each filter. Filters that result in larger decreases in the number of remaining clinical trials in the set of potentially relevant clinical trials may be ranked higher than filters that result in smaller decreases (or no reduction) in the number of remaining clinical trials in the set of potentially relevant clinical trials. In some embodiments, the highest ranked filter (e.g., the filter that results in the largest decrease in the number of remaining clinical trials in the set) may be considered the filter that is most valuable in dividing the set of potentially relevant clinical trials to a focused set of trials for presentation to the user.

In some embodiments, trial recommendation engine 144 may determine, for a trial remaining in a filtered set of clinical trials, a likelihood that the patient will complete each trial. The determination of the likelihood of successful completion may be performed based on completion rates of similar patients in similar trials. For a first trial in the filtered set of clinical trials, trial recommendation engine may compare the characteristics of the first trial to clinically similar trials that have previously been performed. These characteristics may include, for example, a frequency of visits, a distance between the patient's location and the institution conducting the trial, and other information that may be used as proxies for a likelihood of successful completion of the clinical trial. Clinically similar trials may, for example, include trials that target the same condition and the same stage of the condition under treatment with similar eligibility and disqualifying conditions. Trial recommendation engine 144 can identify clinically similar patients (e.g., patients with similar conditions being treated in similar manners prior to participating in a clinical trial) enrolled in the clinically similar trials and determine whether the clinically similar patients successfully completed the clinically similar trials. In some embodiments, if the percentage of clinically similar patients completing previously performed clinically similar trials exceeds a first threshold value, the trial in the filtered set of trials may remain in the filtered set of trials and, in some embodiments, may be displayed in user interface 122 in a prioritized position. If the percentage of clinically similar patients completing clinically similar trials falls below a second threshold value, the trial may be removed from the filtered set of trials or may be deprioritized in a display of the filtered set of clinical trials in user interface 122.

While model trainer 130, application server 140, clinical trial data store 150, patient data store 160, and user activity data store 170 are illustrated as separate components in FIG. 1, it should be recognized that model trainer 130, application server 140, clinical trial data store 150, and patient data store 160 may be implemented on any number of computing systems, either as one or more standalone systems or in a distributed environment.

Figure 2:
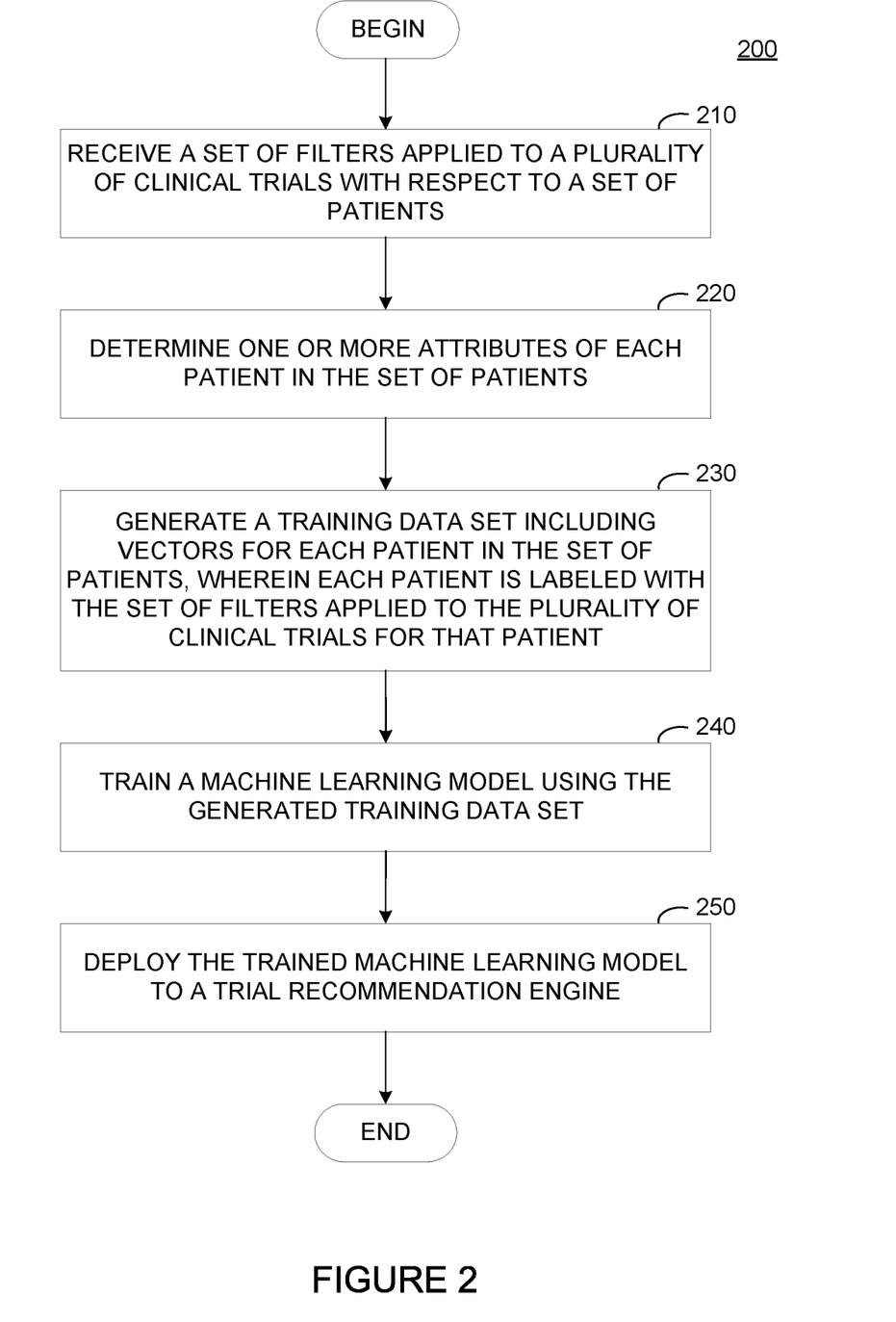
FIG. 2 illustrates example operations for training a machine learning model for recommending filters to apply to clinical trial search results, according to one embodiment.

FIG. 2 illustrates example operations that may be performed to train a machine learning model for recommending filters to apply to a base result set of potentially relevant clinical trials for a patient to refine the base result set, according to an embodiment.

As illustrated, operations 200 begin at block 210, where a machine learning model trainer (e.g., recommendation engine trainer 134 illustrated in FIG. 1) receives a set of filters applied to a plurality of clinical trials with respect to a set of patients. The set of filters may include a plurality of subsets of filters applied to base result sets of potentially relevant clinical trials, and each subset may be associated with a specific patient. Generally, each subset of filters may reflect filters applied by a clinician or other healthcare professional at a first institution, and each subset of filters need not be applied to base result sets of potentially relevant clinical trials by the same clinician. By utilizing filtering activity generated by multiple clinicians or healthcare professionals at a given institution, embodiments of the present disclosure may learn to identify relevant filters for a given class of patient based on the filtering preferences of clinicians throughout an organization (e.g., to reflect organizational preferences in identifying clinical trials to enroll patients in). In some embodiments, the system may receive additional information about the clinician or healthcare professional associated with each subset of filters (i.e., the clinician treating the patient for whom a search for potentially relevant clinical trials was initiated), which may additionally be used to train the machine learning model for recommending filters to apply to a base result set of potentially relevant clinical trials.

At block 220, recommendation engine trainer 134 determines one or more attributes of each patient in the set of patients. The attributes may include information extracted from patient medical history information in patient data store 160 that may be used to identify which clinical trials are potentially relevant for a given patient (and thus should be considered for inclusion in a set of trials returned by trial recommendation engine 144) and which clinical trials are not relevant for the patient (and thus may not be considered for inclusion in a set of trials returned by trial recommendation engine 144). Patient attributes that may be used to determine whether clinical trials are potentially relevant include, but are not limited to, the disease or condition the patient is being treated for, the stage of the disease or medical condition (if applicable), previous medical procedures undertaken to treat the disease or medical condition, and medications prescribed to the patient to treat the disease or medical condition, as well as other attributes that may be of relevance.

At block 230, recommendation engine trainer 134 generates a training data set including vectors for each patient in the set of patients. Each vector may represent a search session performed to identify potentially relevant clinical trials for a specific patient. The features of each vector may include the attributes determined for a specific patient at block 220, and the labels of each vector may include the one or more filters applied by a clinician to refine a set of potentially relevant clinical trials for the patient.

At block 240, recommendation engine trainer 134 trains a machine learning model using the generated training data set. In some embodiments, recommendation engine trainer 134 may train the machine learning model using supervised learning techniques, where the training data set generated at block 230 includes a first set of labeled data used to train the machine learning model and a second set of labeled data used to verify the training of the machine learning model. After training the machine learning model using the first data set, recommendation engine trainer 134 can request a recommended set of filters for one or more patient records in the second set of data in the training data set (i.e., the unlabeled data in the training data set) and return the recommended set filters for analysis. If the recommended set of filters substantially matches the set of filters a clinician applied to a set of potentially relevant clinical trials for the patient (which may be known a priori), no further action need be taken to train the machine learning model. If, however, the recommended set of filters diverges from the set of filters the clinician applied for to the set of potentially relevant clinical trials for the patient (e.g., the recommended set of filters includes filters that were not applied and do not appear to be relevant to the condition the patient was being treated for), the machine learning model may be refined through additional training and correction.

At block 250, recommendation engine trainer 134 deploys the trained machine learning model to a trial recommendation engine (e.g., trial recommendation engine 144 executing on application server 140).

Figure 3:
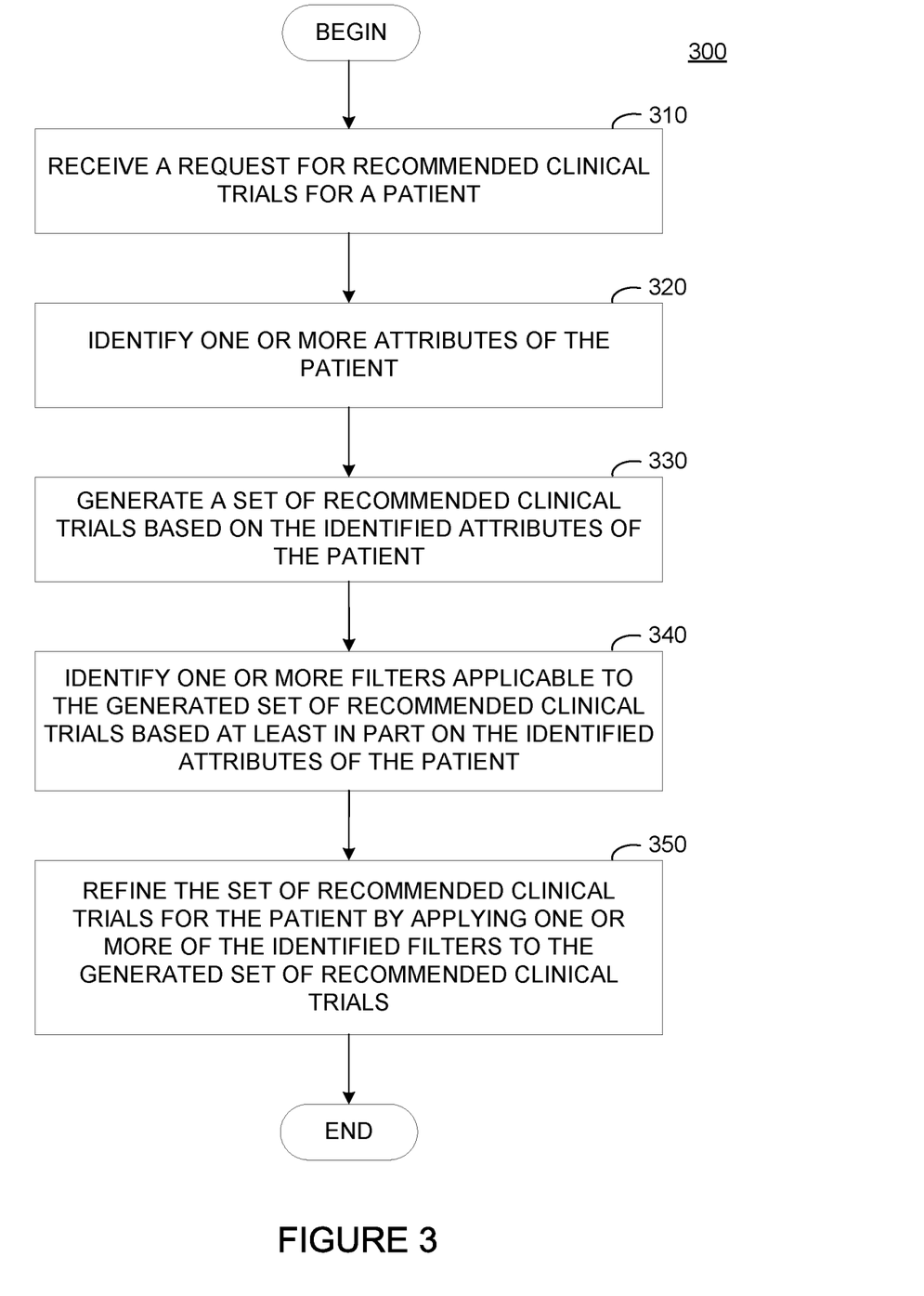
FIG. 3 illustrates example operations for recommending filters to apply to clinical trial search results based on a machine learning model, according to one embodiment.

FIG. 3 illustrates example operations for recommending filters to apply to searches for potentially relevant clinical trials for a patient using a trained machine learning model, according to an embodiment.

As illustrated, operations 300 begin at block 310, where a trial recommendation engine (e.g., trial recommendation engine 144 illustrated in FIG. 1) receives a request for recommended clinical trials for a patient. The request may include, for example, information identifying the patient, information identifying the clinician and/or institution the clinician is affiliated with, and other information that may be used as input into a trained machine learning model for recommending filters to apply to search results generated by processing the request.

At block 320, trial recommendation engine 144 identifies one or more attributes of the patient. In some embodiments, the one or more attributes of the patient may be extracted from information included in the request for recommended clinical trials received at block 310. In some embodiments, the one or more attributes of the patient may be extracted from information retrieved from patient data store 160 using a patient identifier or other identifying information included in the request received at block 310. The one or more attributes of the patient may include attributes previously determined to be relevant to identifying clinical trials that are of potential relevance to the patient. These attributes may include, without limitation, information about the disease the patient is being treated for, the stage of the disease, periodicity trends in visiting clinicians for treatments, previously performed procedures undertaken to treat the disease, prescription medication the patient is taking to treat the disease, and the like.

At block 330, trial recommendation engine 144 generates a set of recommended clinical trials for the patient based, at least in part, on the identified attributes of the patient. As discussed above, trial recommendation engine 144 may use a first machine learning model that matches a patient to a base result set of potentially relevant clinical trials based on clinical trials that similar patients have previously been enrolled into.

At block 340, trial recommendation engine 144 identifies one or more filters applicable to the generated set of recommended clinical trials based at least in part on the identified attributes of the patient. As discussed, trial recommendation engine 144 may identify the one or more filters applicable to the generated set of recommended clinical trials for the patient by providing at least the identified attributes of the patient to a second machine learning model trained to identify filters to apply to the base result set of potentially relevant clinical trials based on previous filtering activity performed by other clinicians for clinically similar patients. Trial recommendation engine 144 may return a probability distribution over a set of filters that can be applied to the base result set, where the probability value for each filter represents a likelihood that each filter will be relevant for filtering the base result set for the patient (e.g., that clinicians treating clinically similar patients have applied a particular filter to search results). The filters having the highest probability scores may be prioritized (e.g., ranked higher) in recommendations delivered to a user of application 142, while filters having lower probability scores may be deprioritized (e.g., ranked lower) or not included at all.

At block 350, trial recommendation engine 144 refines the set of recommended clinical trials for the patient by applying one or more of the identified filters to the generated set of recommended clinical trials. As discussed, the one or more filters applied to the generated set of recommended clinical trials may include, for example, filters having probability scores over a threshold level. In some embodiments, the filters applied to the generated set of recommended clinical trials may be identified based on a number of search results remaining in the set of recommended clinical trials for the patient, where filters that reduce the number of remaining search results by larger numbers are prioritized (and, in some cases, automatically applied) over filters that reduce the number of remaining search results by smaller numbers and filters that do not reduce the number of remaining search results at all.

Figure 4:
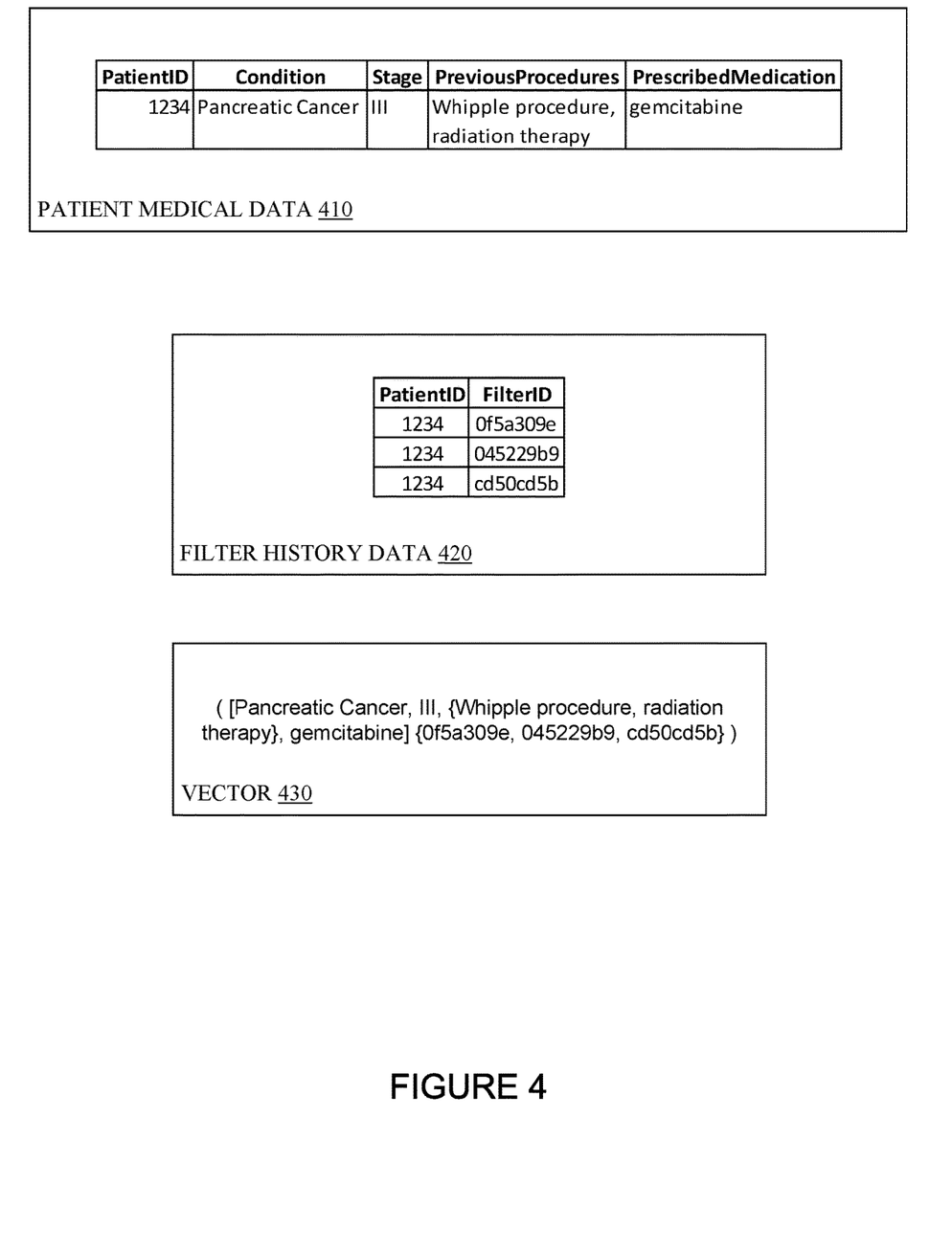
FIG. 4 illustrates an example mapping between patient medical records and clinical trial characteristics used in training a machine learning model for recommending filters to apply to a set of clinical trial search results, according to one embodiment.

FIG. 4 illustrates an example of patient medical data and filter history data used to generate vectors for training a machine learning model that generates predictive scores representing a likelihood that a user will find a particular filter to be useful in refining a set of potentially relevant clinical trials, according to an embodiment.

As illustrated, patient medical data 410 may include various pieces of information associated with a patient that a clinician is attempting to enroll in one or more clinical trials. The patient medical data may include, as illustrated, a patient identifier, information about the condition or disease under treatment, the stage of the condition or disease under treatment, previous procedures performed to treat the condition or disease, and prescribed medications for treating the condition or disease. For example, as illustrated in patient medical data 410, a patient with the patient identifier of 1234 is being treated for Stage III pancreatic cancer, has undergone the Whipple procedure and radiation therapy for treatment, and is currently receiving gemcitabine for treatment. This information may be used as features of a vector associating the patient medical data with filter history data such that a machine learning model can identify clinically similar patients (e.g., in this example, patients who are also being treated for Stage III pancreatic cancer, having undergone the Whipple procedure and radiation therapy and been prescribed gemcitabine for treatment), as discussed in further detail above. While the data illustrated in FIG. 4 is shown as textual information, it should be recognized that other forms of data identifying the condition or disease under treatment, the stage of the condition or disease under treatment, previous procedures performed to treat the condition or disease, and prescribed medications for treating the condition or disease may be included in patient medical data 410. For example, the information about the condition or disease under treatment may be represented by one or more ICD (International Classification of Diseases) codes used across institutions, and information about procedures and medications taken to treat a condition or disease may be represented by unique identifiers.

Filter history data 420 generally includes information identifying the one or more filters a clinician applied to a base result set of potentially relevant clinical trials for the patient described in patient medical data 410. Each filter that can be applied to the base result set may be associated with a unique identifier (e.g., a Globally Unique ID, a hash value, etc.). As illustrated in this example, the clinician treating the patient with the patient identifier of 1234 has applied three filters to the search results retrieved through application 142: a first filter with a filter ID of "0f5a309e", a second filter with a filter ID of "045229b9", and a third filter with a filter ID of "cd50cd5b".

Vector 430 represents training data that may be used to train a machine learning model to recommend filters to apply to search results for potentially relevant clinical trials. Vector 430 generally includes the patient medical data 410 as feature data and filter history data 420 as label data. The patient medical data 410 is mapped to the filter history data 420 to reflect that for a patient with a specified set of characteristics, a clinician filtered search results using a specific set of filters.

Figure 5:
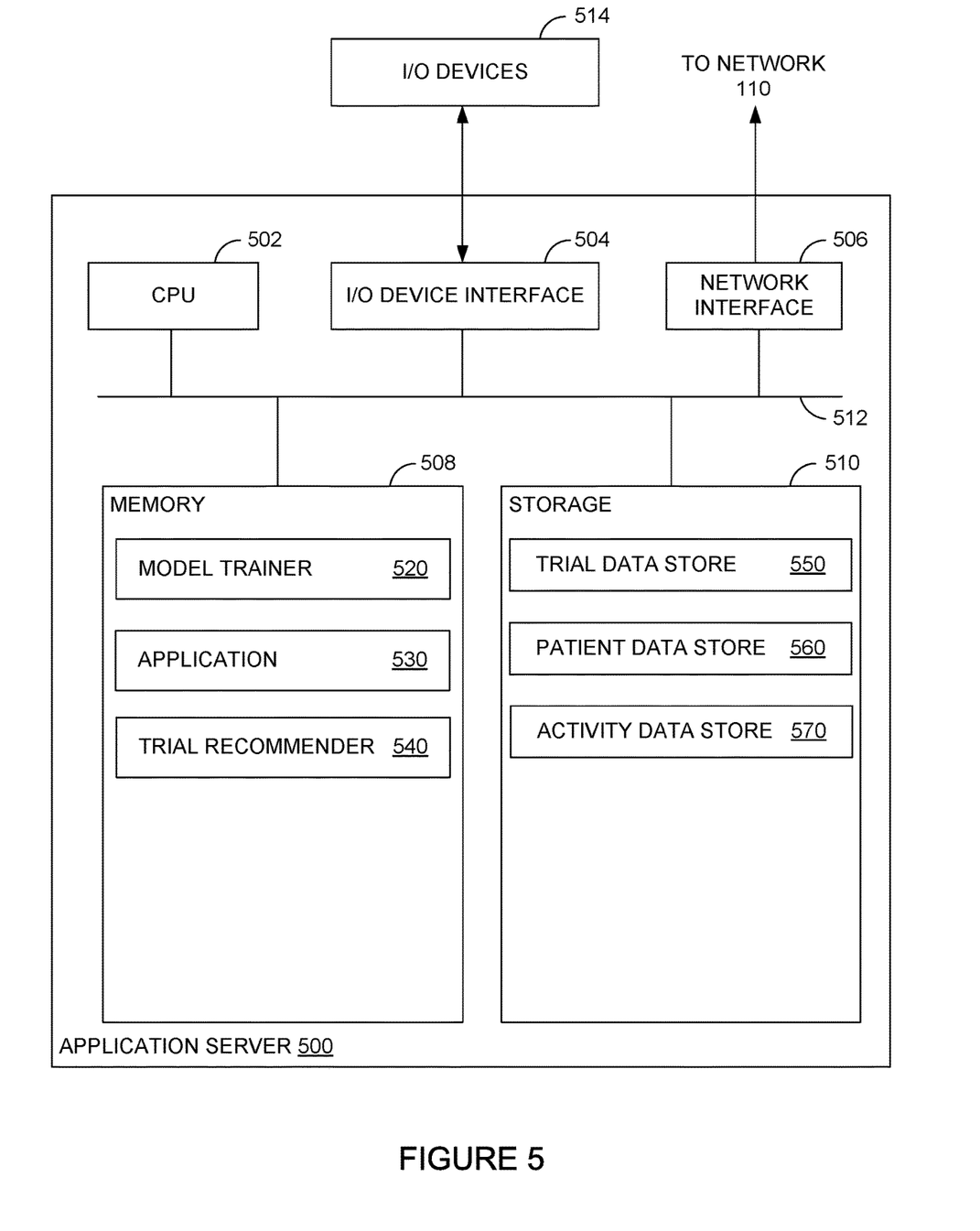
FIG. 5 illustrates an example system in which aspects of the present disclosure may be performed.

FIG. 5 illustrates an example application server 500 that recommends, to a clinician, filters to apply to a base result set of potentially relevant clinical trials for a patient using a machine learning model, according to an embodiment. As shown, application server 500 includes, without limitation, a central processing unit 502, one or more I/O device interfaces 504, which may allow for the connection of various I/O devices 514 (e.g., keyboards, displays, mouse devices, pen input, etc.) to the entity analytics system 500, network interface 506, a memory 508, storage 510, and an interconnect 512.

CPU 502 may retrieve and execute programming instructions stored in the memory 508. Similarly, the CPU 502 may retrieve and store application residing in the memory 508. The interconnect 512 transmits programming instructions and application data among the CPU 502, I/O device interface 504, network interface 506, memory 508, and storage 510. CPU 502 is included to be representative of a single CPU, multiple CPUs, a single CPU having multiple processing cores, and the like. Additionally, the memory 508 is included to be representative of a random access memory. Furthermore, the storage 510 may be a disk drive. Although shown as a single unit, the storage 510 may be a combination of fixed and/or removable storage devices, such as fixed disc drives, solid state drives, removable memory cards or optical storage, network attached storage (NAS), or a storage area-network (SAN).

As illustrated, memory 508 includes a model trainer 520, application 530, and trial recommender 540. Model trainer 520 is generally configured to retrieve at least patient medical data from patient data store 560 and activity data store 570 to generate a training data set usable by model trainer 520 to train one or more machine learning models. As discussed, the training data set may include a plurality of vectors in which patient characteristics (e.g., the condition under treatment, the stage of the condition under treatment, procedures performed to treat the condition, medications prescribed to treat the condition, etc.) are associated with filters applied by a clinician to refine a base set of potentially relevant clinical trials for the patient. Based at least in part on the training data set, model trainer 520 trains one or more machine learning models for recommending filters to apply to a base set of potentially relevant clinical trials based on patient characteristics and, in some embodiments, clinician and institutional affiliation information, and other data that may be useful in refining the base set of potentially relevant clinical trials for a patient.

Application 530 generally allows a user (e.g., a clinician treating a patient) to search for potentially relevant clinical trials that may be relevant to a patient the user is treating. To search for potentially relevant clinical trials from trial data store 550, a user transmits a request to application 530 (e.g., via network interface 506 from a remote computing system)

including information about the patient being treated. Application 530 may pass the information about the patient being treated to trial recommender 540, which, as discussed above, is configured to identify potentially relevant clinical trials from the medical information about the patient and generate a base result set of the identified potentially relevant clinical trials. Trial recommender 540 may be further configured to provide the information about the patient being treated, and optionally other information (e.g., clinician specialty, institutional affiliation, etc.) to a machine learning model configured to identify filters that may be used to refine the base result set of potentially relevant clinical trials. The machine learning model may return a probability distribution over a set of filters that can be applied to the base result set, where the probability value associated with a particular filter represents a likelihood that the filter would be of relevance to a clinician based on the filtering activities performed by other clinicians treating clinically similar patients. In some embodiments, some filters may be automatically applied to the base result set to refine the set of potentially relevant clinical trials. In some embodiments, trial recommender 540 may further rank potentially relevant filters for presentation to a user of application 530 based, for example, on a number of remaining results in the refined set of potentially relevant clinical trials after application of a filter.

Storage 510, as illustrated, includes trial data store 550, patient data store 560, and activity data store 570. Trial data store 550 generally represents a data repository in which details of previously performed and currently enrolling clinical trials are stored. Each trial stored in trial data store 550 generally includes eligibility and disqualifying criteria for the trial, operational characteristics of the trial, and the like. Patient data store 560 generally stores information about patients enrolled in previously performed trials and information about patients currently under consideration for inclusion in one or more clinical trials. As discussed, the patient information may be used to generate training data sets that are used to train machine learning models to recommend clinical trials for a patient. Activity data store 570 generally stores a history of clinician filtering history for search results retrieved for a given patient. As discussed, the patient information and filtering history may be used to generate the training data sets for training machine learning models to recommend filters to apply to a base result set of potentially relevant clinical trials for the patient to refine the result set.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the foregoing is directed to embodiments of the present invention, other and further embodiments of the invention may be devised without departing from the basic scope thereof, and the scope thereof is determined by the claims that follow.

What is claimed is:

1. A method for cognitive clinical trial filtration, the method comprising:
    receiving a first set of search filters that were applied to a first plurality of clinical trials with respect to a first patient;
    determining one or more attributes of the first patient;
    training a machine learning (ML) model based on the first set of filters and the one or more attributes of the first patient;
    receiving a selection of a second patient;
    determining one or more attributes of the second patient;
    generating a base search result set for the second patient based on the determined one or more attributes of the second patient, the base search result set including a set of potentially relevant clinical trials for the second patient;
    generating a second set of search filters by processing the one or more attributes of the second patient using the trained ML model, wherein the second set of search filters comprise search filters recommended for searching for relevant clinical trials for the second patient based on filters used to search for relevant clinical trials for historical patients having similar attributes to the determined one or more attributes of the second patient, and wherein the second set of search filters comprise search filters having a highest probability of relevance in a probability distribution over a universe of candidate search filters; and
    generating a refined search result set by applying the generated second set of search filters to the base search result set.

2. The method of claim 1, the method further comprising:
    determining one or more characteristics of at least a first trial of the first plurality of clinical trials, wherein the one or more characteristics includes at least one of: a phase of the trial or a type of the trial; and
    training the ML model based on the one or more characteristics of the first trial.

3. The method of claim 1, the method further comprising:
    determining operational data for at least a first trial of the first plurality of clinical trials, wherein the operational data includes at least one of: a site associated with the trial or one or more other trials that are also associated with the site; and
    training the ML model based on the operational data for the first trial.

4. The method of claim 1, wherein generating the refined search result set comprises automatically applying at least a first filter of the second set of search filters to a list of potential clinical trials for the second patient.

5. The method of claim 4, the method further comprising:
determining a subset of the list of potential clinical trials that remain after application of the first filter;
selecting at least a second filter of the second set of search filters to apply to the subset of the list of potential clinical trials, based on determining that the second filter is most valuable to further divide the subset of the list of potential clinical trials.

6. The method of claim 5, wherein determining that the second filter is most valuable to further divide the subset of the list of potential clinical trials comprises determining that the second filter will reduce a number of potential clinical trials remaining in the subset of the list of potential clinical trials to a minimum amount, as compared to other filters in the second set of search filters.

7. The method of claim 1, the method further comprising:
determining, for at least a first potential trial of a list of potential clinical trials for the second patient, a likelihood that the second patient will complete the first potential trial.

8. The method of claim 7, wherein determining the likelihood that the second patient will complete the first potential trial comprises:
identifying one or more prior studies that are clinically similar to the first potential trial;
identifying, for at least a first prior study of the one or more prior studies, one or more prior patients that are clinically similar to the second patient and participated in the first prior study; and
determining whether the one or more prior patients successfully completed the first prior study.

9. The method of claim 1, wherein the first set of search filters were applied by a first healthcare professional at a first institution, and wherein training the ML model is further based on data collected from at least one other healthcare professional at the first institution.

10. The method of claim 1, wherein the first set of search filters were applied by a first healthcare professional, and wherein training the ML model is further based on data collected from the first healthcare professional.

11. A system, comprising:
a processor; and
a memory having instructions stored thereon which, when executed by the processor, performs an operation for cognitive clinical trial filtration, the operation comprising:
receiving a first set of search filters that were applied to a first plurality of clinical trials with respect to a first patient;
determining one or more attributes of the first patient;
training a machine learning (ML) model based on the first set of filters and the one or more attributes of the first patient;
receiving a selection of a second patient;
determining one or more attributes of the second patient;
generating a base search result set for the second patient based on the determined one or more attributes of the second patient, the base search result set including a set of potentially relevant clinical trials for the second patient;
generating a second set of search filters by processing the one or more attributes of the second patient using the trained ML model, wherein the second set of search filters comprise search filters recommended for searching for relevant clinical trials for the second patient based on filters used to search for relevant clinical trials for historical patients having similar attributes to the determined one or more attributes of the second patient, and wherein the second set of search filters comprise search filters having a highest probability of relevance in a probability distribution over a universe of candidate search filters; and
generating a refined search result set by applying the generated second set of search filters to the base search result set.

12. The system of claim 11, wherein the operation further comprises:
determining one or more characteristics of at least a first trial of the first plurality of clinical trials, wherein the one or more characteristics includes at least one of: a phase of the trial or a type of the trial; and
training the ML model based on the one or more characteristics of the first trial.

13. The system of claim 11, wherein the operation further comprises:
determining operational data for at least a first trial of the first plurality of clinical trials, wherein the operational data includes at least one of: a site associated with the trial or one or more other trials that are also associated with the site; and
training the ML model based on the operational data for the first trial.

14. The system of claim 11, wherein generating the refined search result set comprises: automatically applying at least a first filter of the second set of search filters to a list of potential clinical trials for the second patient.

15. The system of claim 11, wherein the operation further comprises:
determining, for at least a first potential trial of a list of potential clinical trials for the second patient, a likelihood that the second patient will complete the first potential trial by:
identifying one or more prior studies that are clinically similar to the first potential trial;
identifying, for at least a first prior study of the one or more prior studies, one or more prior patients that are clinically similar to the second patient and participated in the first prior study; and
determining whether the one or more prior patients successfully completed the first prior study.

16. A non-transitory computer-readable storage medium having instructions stored thereon which, when executed by a processor, performs an operation for cognitive clinical trial filtration, the operation comprising:
receiving a first set of search filters that were applied to a first plurality of clinical trials with respect to a first patient;
determining one or more attributes of the first patient;
training a machine learning (ML) model based on the first set of filters and the one or more attributes of the first patient;
receiving a selection of a second patient;
determining one or more attributes of the second patient;
generating a base search result set for the second patient based on the determined one or more attributes of the second patient, the base search result set including a set of potentially relevant clinical trials for the second patient;
generating a second set of search filters by processing the one or more attributes of the second patient using the trained ML model, wherein the second set of search filters comprise search filters recommended for searching for relevant clinical trials for the second patient based on filters used to search for relevant clinical trials for historical patients having similar attributes to the determined one or more attributes of the second patient, and wherein the second set of search filters comprise search filters having a highest probability of relevance in a probability distribution over a universe of candidate search filters; and generating a refined search result set by applying the generated second set of search filters to the base search result set.

17. The computer-readable storage medium of claim 11, wherein the operation further comprises:

determine one or more characteristics of at least a first trial of the first plurality of clinical trials, wherein the one or more characteristics includes at least one of: a phase of the trial or a type of the trial; and train the ML model based on the one or more characteristics of the first trial.

18. The computer-readable storage medium of claim 16, wherein the operation further comprises:

determine operational data for at least a first trial of the first plurality of clinical trials, wherein the operational data includes at least one of: a site associated with the trial or one or more other trials that are also associated with the site; and train the ML model based on the operational data for the first trial.

19. The computer-readable storage medium of claim 16, wherein generating the refined search set comprises: automatically applying at least a first filter of the second set of search filters to a list of potential clinical trials for the second patient.

20. The computer-readable storage medium of claim 16, wherein the operation further comprises:

determine, for at least a first potential trial of a list of potential clinical trials for the second patient, a likelihood that the second patient will complete the first potential trial by:

identifying one or more prior studies that are clinically similar to the first potential trial;

identifying, for at least a first prior study of the one or more prior studies, one or more prior patients that are clinically similar to the second patient and participated in the first prior study; and determining whether the one or more prior patients successfully completed the first prior study.

* * * * *